US005935391A

United States Patent [19]
Nakahigashi et al.

[11] Patent Number: 5,935,391
[45] Date of Patent: *Aug. 10, 1999

[54] METHOD OF MANUFACTURING A TUBE HAVING A FILM ON ITS INNER PERIPHERAL SURFACE AND APPARATUS FOR MANUFACTURING THE SAME

[75] Inventors: Takahiro Nakahigashi; Hajime Kuwahara, both of Kyoto; Hiroshi Fujiyama, Nagayo-machi, all of Japan

[73] Assignee: Nissin Electric Co., Ltd., Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/381,311

[22] Filed: Jan. 31, 1995

[30] Foreign Application Priority Data

Jan. 31, 1994 [JP] Japan .................................. 6-009736
Dec. 26, 1994 [JP] Japan .................................. 6-322576

[51] Int. Cl.⁶ .................................................. C23C 14/34
[52] U.S. Cl. .............................. 204/192.12; 204/298.21; 118/723 E; 118/723 MP; 427/569; 427/571
[58] Field of Search ...................... 204/192.12, 298.21; 118/723 E, 723 MP; 427/569, 571

[56] References Cited

U.S. PATENT DOCUMENTS

| 4,376,025 | 3/1983 | Zega | 204/298.21 X |
| 4,407,713 | 10/1983 | Zega | 204/298.21 X |
| 4,478,703 | 10/1984 | Edamura et al. | 204/298.21 X |
| 4,511,451 | 4/1985 | Sella et al. | 204/298.11 |
| 4,764,398 | 8/1988 | Croitoru et al. | |
| 4,904,362 | 2/1990 | Gaertner et al. | 204/298.21 X |
| 4,960,753 | 10/1990 | Collins et al. | 204/298.21 X |
| 5,272,735 | 12/1993 | Bryan et al. | 204/298.21 X |
| 5,298,137 | 3/1994 | Marshall, III | 204/298.22 X |

FOREIGN PATENT DOCUMENTS

| 0 568 049 A1 | 11/1993 | European Pat. Off. . |
| 62-70578 | 4/1987 | Japan . |
| 62-74083 | 4/1987 | Japan . |
| 2 133 786 | 8/1984 | United Kingdom . |

*Primary Examiner*—Nam Nguyen
*Assistant Examiner*—Steven H. Ver Steeg
*Attorney, Agent, or Firm*—Nikaido Marmelstein Murray & Oram LLP

[57] ABSTRACT

A rod-like electrode is disposed in a vacuum container, a ring-like electrode is disposed around the rod-like electrode, a tube to be processed is disposed such that the tube is substantially continuous to the ring-like electrode, an interior of the vacuum container is set to a predetermined degree of vacuum for deposition, a gas is introduced into a space between the electrodes, an electric power for forming plasma from the gas is applied while applying a magnetic field, and the plasma produced thereby is supplied into the tube. If the deposition material gas is used, the film is formed on the inner peripheral surface of the tube. If the plasma source gas for sputtering is used, a sputtering voltage is applied to a sputtering target disposed inside the tube, so that the film is formed on the inner peripheral surface of the tube by sputtering the target with ions in the plasma.

4 Claims, 4 Drawing Sheets

5,935,391

METHOD OF MANUFACTURING A TUBE HAVING A FILM ON ITS INNER PERIPHERAL SURFACE AND APPARATUS FOR MANUFACTURING THE SAME

BACKGROUND OF THE INVENTION

1. Field of the Invention

The present invention relates to a method of forming a predetermined film on an inner surface of a tube such as various kinds of glass pipes, a capillary tube for cooling water in a nuclear device and a medical catheter for the purpose such as protection of the inner peripheral surface of the tube, and also relates to an apparatus for forming the same.

2. Description of the Background Art

In general, vapor deposition is employed for forming such a film on an inner peripheral surface of a tube.

An example of an apparatus for performing such vapor deposition will be described below with reference to FIG. 4. The apparatus shown in FIG. 4 has a vacuum container 10, in which a tube S4 to be processed (i.e., a tube on which a film is to be deposited) is disposed and held by an unillustrated holder. Inside the tube S4, there is disposed a wire-like or rod-like deposition material 90 having the same length as the tube S4. Opposite ends of the deposition material 90 are connected to a DC power source 60. An exhaust device 110 is connected to the container 10.

According to this apparatus, the exhaust device 110 operates to set an interior of the container 10 to a predetermined degree of vacuum, and the DC power source 60 applies a DC power to the opposite ends of the deposition material 90. Thereby, the deposition material 90 is heated and is vacuum-deposited onto the inner peripheral surface of the tube S4, so that an intended film is formed on the inner peripheral surface of the tube S4.

However, according to the deposition by the vacuum deposition apparatus described above, when the tube S4 has a small inner diameter, the deposition material 90 must has a small diameter corresponding to it, so that the deposition material is liable to break when it is evaporated by application of the electric power. In order to continue the deposition of the film on the inner peripheral surface of the tube, the broken deposition material must be replaced with new one. For this replacement, the container 10 must be temporarily set to the atmospheric pressure for mounting a new deposition material, and, after the mounting, the container 10 must be set to the predetermined degree of vacuum, which requires a time-consuming operation and hence reduces a productivity.

A plasma chemical vapor deposition (plasma CVD) method is a method allowing supply of a deposition material without breaking the vacuum state. This method, however, cannot generate plasma inside the tube, and cannot form a film on the inner peripheral surface of the tube. If the plasma is generated outside the tube, the plasma cannot be supplied into the tube.

SUMMARY OF THE INVENTION

Accordingly, it is an object of the invention to provide a method and an apparatus which can provide a tube having a film on its inner peripheral surface with good productivity, and more specifically can uniformly or substantially uniformly form the film on the inner peripheral surface even if the tube has a small inner diameter.

The inventors have studied to achieve the aforementioned object, and have found that, even if a tube to be processed has a small diameter, plasma can be supplied to an interior of the tube by such a manner that the plasma is generated at the vicinity of an opening of the tube to be processed, and a magnetic field having such a directional property is produced that cooperates with an electric field, which is produced by an electric power applied for producing the plasma, to produce an electromagnetic force rotating and moving spirally the plasma along the tube. The invention has been developed based on the above founding.

In order to achieve the above object, the invention provides the following two methods of manufacturing a tube having a film on its inner peripheral surface, and also provides apparatuses for manufacturing a tube having a film on its inner peripheral surface by performing the above methods.

According to the invention for achieving the above object, a first method of manufacturing a tube having a film on its inner peripheral surface includes the steps of disposing a rod-like electrode in a vacuum container, disposing a ring-like electrode around the rod-like electrode with a predetermined space therebetween, disposing a tube to be processed such that the tube is substantially continuous to the ring-like electrode, setting an interior of the vacuum container to a predetermined degree of vacuum for deposition, introducing a deposition material gas into a space between the rod-like and ring-like electrodes, applying an electric power for forming plasma from the gas while applying a magnetic field, and supplying the plasma produced thereby into the tube for forming the film on the inner peripheral surface of the tube in the plasma.

According to the invention for achieving the above object, a second method of manufacturing a tube having a film on its inner peripheral surface includes the steps of disposing a rod-like electrode in a vacuum container, disposing a ring-like electrode around the rod-like electrode with a predetermined space therebetween, disposing a rod-like sputtering target receiving a voltage on an extension of the rod-like electrode, disposing a tube to be processed such that the tube is located around the sputtering target and is substantially continuous to the ring-like electrode, setting an interior of the vacuum container to a predetermined degree of vacuum for deposition, introducing a plasma source gas into a space between the rod-like and ring-like electrodes, applying an electric power for forming plasma from the gas while applying a magnetic field, supplying the plasma thus produced into the tube, applying a sputtering voltage to the sputtering target for sputtering the sputtering target to form the film on the inner peripheral surface of the tube.

An apparatus (i.e., first manufacturing apparatus) for manufacturing a tube having a film on its inner peripheral surface, which is used for executing the aforementioned first method of manufacturing the tube having the film on its inner peripheral surface, includes a vacuum container, a rod-like electrode disposed in the container and a ring-like electrode disposed in the container and around the rod-like electrode with a predetermined space therebetween, a holder holding a tube to be processed such that the tube is substantially continuous to the ring-like electrode, means for introducing a deposition material gas into a space between the rod-like and ring-like electrodes, means for applying an electric power between the electrodes for producing plasma from the gas, and means for applying a magnetic field to the plasma so as to supply the plasma generated between the electrodes into the tube held by the holder.

An apparatus (i.e., second manufacturing apparatus) for manufacturing a tube having a film on its inner peripheral surface, which is used for executing the aforementioned second method of manufacturing the tube having the film on its inner peripheral surface, includes a vacuum container, a rod-like electrode disposed in the container and a ring-like electrode disposed in the container and around the rod-like electrode with a predetermined space therebetween, means for supporting a rod-like sputtering target on an extension of the rod-like electrode, a holder for holding a tube to be processed around the sputtering target supported by the supporting means such that the tube is substantially continuous to the ring-like electrode, means for introducing a plasma source gas into a space between the rod-like and ring-like electrodes, means for applying an electric power between the electrodes for producing plasma from the gas, means for applying a magnetic field to the plasma so as to supply the plasma generated between the electrodes into the tube held by the holder, and means for applying a sputtering voltage to the sputtering target.

The magnetic field applied in the first and second methods and the first and second apparatuses of the invention has such a directional property that cooperates with a current caused by the electric power applied between the rod-like and ring-like electrodes to produce an electromagnetic force which acts to supply and move spirally the plasma into the tube.

In this specification, the magnetic field having the directional property is referred to as "longitudinal magnetic field".

The second method and apparatus of the invention use, as the plasma source gas, an inert gas such as a helium (He) gas, a neon (Ne) gas, an argon (Ar) gas, a krypton (Kr) gas or a xenon (Xe) gas, or an active gas such as a nitrogen ($N_2$) gas, an ammonia ($NH_3$) gas or an oxygen ($O_2$) gas. One or more of these gases can be used.

In the second method and apparatus described above, the rod-like sputtering target has a length allowing formation of the film at an intended portion of the inner peripheral surface of the tube, and, for example, has a length substantially equal to the length of the tube if the film is to be formed on the whole inner peripheral surface of the tube.

In the second method and apparatus described above, the sputtering target is made of a material allowing formation of the intended film on the inner peripheral surface of the tube by the sputtering, and, for example, may be made of single kind of metal selected from various kinds of metal, single kind of non-metal or compounds of them.

In the second method and apparatus described above, the sputtering voltage applied to the sputtering target is generally negative if the sputtering target is made of an electrically conductive material, and may be a radio-frequency voltage if the sputtering target is made of an insulator.

If the sputtering target is made of the electrically conductive material, the voltage applied to the sputtering target may be equal to the voltage applied to the rod-like electrode, or may be different from it. If equal, the sputtering target may be disposed in contact with the rod-like electrode, and the means for applying the electric power between the rod-like and ring-like electrodes for producing the plasma may be used also as the means for applying the voltage to the sputtering target. If different, the sputtering target is electrically isolated from the rod-like electrode, and the means for applying the power between the rod-like and ring-like electrodes is provided independently from the means for applying the voltage to the sputtering target, so that the power for generating the plasma is controlled independently from the voltage for sputtering.

If the sputtering target is made of the insulator, an electrode is disposed inside the target, to which a radio-frequency is applied. The electrode inside the target may have a length equal to that of the sputtering target.

In the first manufacturing method and apparatus for manufacturing the tube having the film on its inner peripheral surface according to the invention, the deposition material gas is introduced into the space between the rod-like electrode and the ring-like electrode disposed around the rod-like electrode with the predetermined space therebetween, and the power for producing the plasma is applied between the electrodes so that the plasma is formed from the gas. Meanwhile, a longitudinal magnetic field is applied to the inside of the ring-like electrode. The longitudinal magnetic field cooperates with a current generated by the electric field applied as described above to rotate and move spirally the plasma generated by the power application along the tube disposed substantially continuously to the ring-like electrode, so that the plasma is supplied to and diffused at the interior of the tube. In this manner, the film is deposited uniformly or substantially uniformly on the inner peripheral surface of the tube in the plasma. Further, the deposition material gas can be added into the container, if necessary, without breaking the vacuum in the container performing the deposition.

In the second manufacturing method and apparatus for manufacturing the tube having the film on its inner peripheral surface according to the invention, the plasma source gas is introduced into the space between the rod-like electrode and the ring-like electrode disposed around the rod-like electrode with the predetermined space therebetween, and the power for producing the plasma is applied between the electrodes so that the plasma is formed from the gas. Meanwhile, a longitudinal magnetic field is applied to the inside of the ring-like electrode. The longitudinal magnetic field cooperates with a current generated by the electric field applied as described above to rotate and move spirally the plasma generated by the power application along the tube disposed substantially continuously to the ring-like electrode, so that the plasma is supplied to and diffused at the interior of the tube.

Meanwhile, if the sputtering target is made of the electrically conductive material, a voltage (generally, negative voltage) of a polarity opposite to the charge of ions contributing to the sputtering in the plasma is applied to the rod-like sputtering target disposed inside the tube, so that the ions are pulled toward the sputtering target for continuously sputtering the target. If the sputtering target is made of the electrical insulator, ions in the plasma moved into the tube tend to charge the surface thereof. However, the radio-frequency voltage applied to the electrode and others disposed inside the sputtering target suppresses accumulation of the electric charges, and the ions continuously sputter the target. In either case, the sputtering particles are deposited uniformly or substantially uniformly on the inner surface of the tube to form the film.

In the second method and apparatus, if an inert gas is used as the plasma source gas, the film consisting of atoms forming the sputtering target is deposited on the inner peripheral surface of the tube. If an active gas such as a nitrogen gas, an ammonia gas or an oxygen gas, a film made of, e.g., nitride or oxide of the atoms forming the sputtering target is deposited on the inner peripheral surface of the tube.

If the rod-like sputtering target has a length substantially equal to that of the tube to be processed, the film is formed on the whole inner peripheral surface of the tube.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
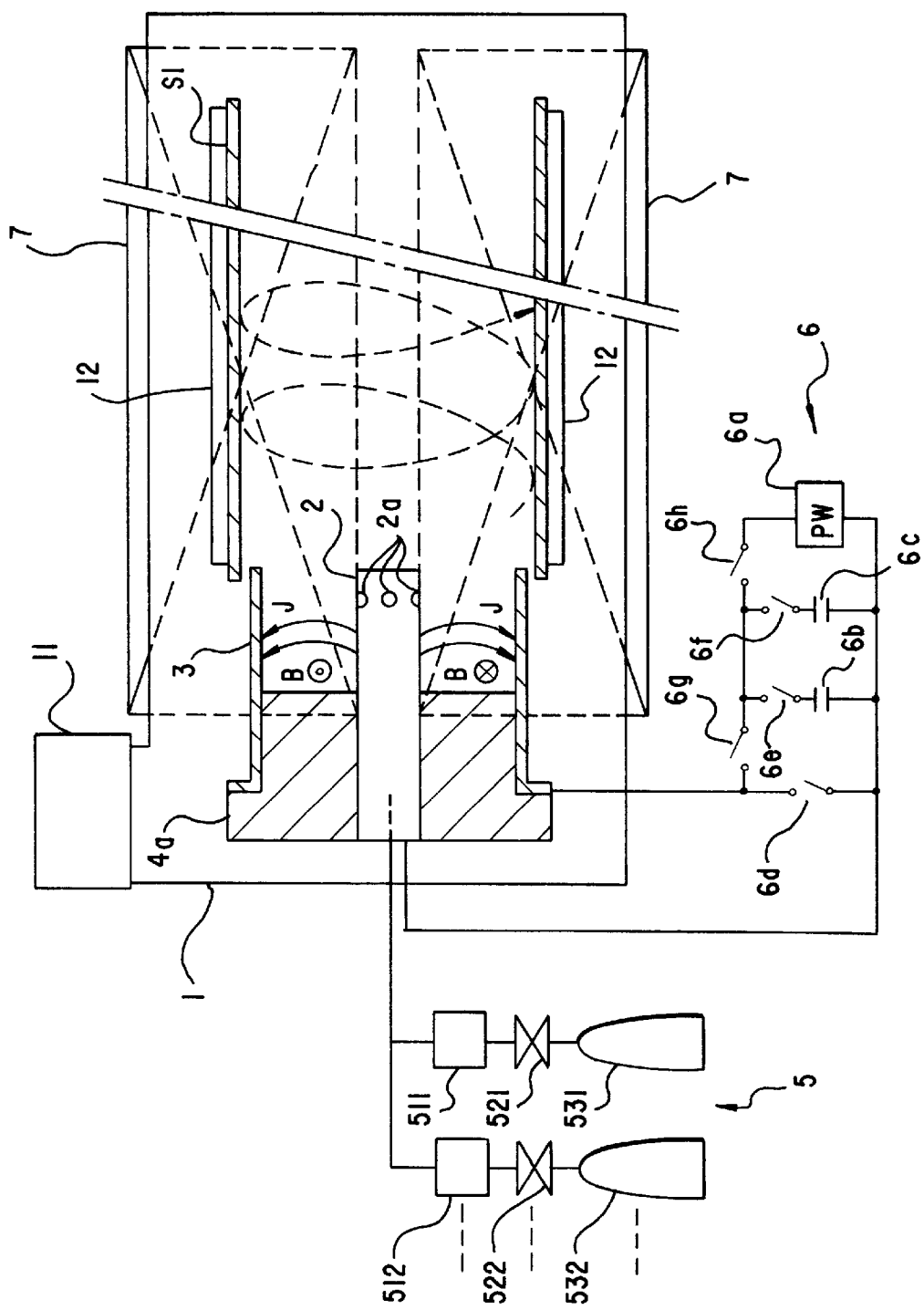
FIG. 1 is a fragmentary cross section schematically showing a structure of an example of an apparatus for manufacturing a tube having a film on its inner peripheral surface.

Referring to FIG. 1, an apparatus for manufacturing a tube having a film on its inner peripheral surface includes a vacuum container 1, in which a central electrode 2 of a hollow rod-like form is disposed and also a ring-like electrode 3 is disposed around the rod-like electrode 2 with a predetermined space therebetween. The ring-like electrode 3 has an outer diameter slightly smaller than an inner diameter of a tube S1 to be processed. A ring-like insulating spacer 4a is fitted between the electrodes 2 and 3. These members are supported in the vacuum container 1 by an unillustrated supporting member or holder. The central electrode 2 is connected via a piping to a gas supply 5 of a deposition material gas, and is provided at its periphery with a plurality of equally spaced gas nozzles 2a through which the deposition material gas is ejected. The gas supply 5 includes one or more gas sources 531, 532, . . . of deposition material gases connected to valves 521, 522, . . . and mass-flow controllers 511, 512, . . . , respectively. A power supply 6 is connected to the electrodes 2 and 3. The power supply 6 includes a DC power source 6a having one end connected to the electrode 2 and the other end connected to the electrode 3 via a charging switch 6h and an on/off switch 6g, and also includes a capacitor 6b for starting discharging, a capacitor 6c for controlling a deposition rate and a switch 6d for a crowbar circuit which are connected in parallel to the aforementioned circuits. The power supply 6 further includes a switch 6e for starting discharging connected in serial to the capacitor 6b, and a switch 6f for controlling the deposition rate connected in serial to the capacitor 6c. The power supply 6 may be replaced with a power supply circuit including a semiconductor switch such as an inverter. A solenoid 7 is disposed around the vacuum container 1, and the coil is connected to an unillustrated DC power source for applying a longitudinal magnetic field in a direction indicated by arrows B in the figure. The solenoid 7 may be replaced with a permanent magnet. An exhaust device 11 is connected to the vacuum container 1. In front of the electrode 3, there is disposed a support holder 12 for holding the tube S1. The support holder 12 is held in the container 1 by an unillustrated member.

According to this apparatus, the solenoid 7 generates a longitudinal magnetic field in the vacuum container 1 as indicated by B in the figure. Initially, all the switches in the power supply 6 are open, and the tube S1 is transferred into the vacuum container 1. After the tube S1 is held by the holder 12 such that the tube S1 is substantially continuous to the ring-like electrode 3, the exhaust device 11 is operated to set the interior of the vacuum chamber 1 to a predetermined degree of vacuum. Then, the film deposition gas is introduced from the gas supply 5 and is ejected through the gas nozzles 2a of the central electrode 2 into a space between the electrodes 2 and 3. Also, the charge starting switch 6e, deposition rate control switch 6f and switch 6h are closed, so that the DC power source 6a supplies the power to charge the charge starting capacitor 6b and deposition rate control capacitor 6c. The charging is terminated by opening the switches 6e, 6f and 6h. Then, the switch 6g and charge starting switch 6e are closed, and thus the charge starting capacitor 6b operates to apply the DC power from the central electrode 2 toward the ring-like electrode 3, so that the plasma starts to be generated from the deposition material gas already introduced. Thereafter, the plasma is maintained by the application of the power from the deposition rate control capacitor 6c, during which the switch 6e is opened and the deposition rate control switch 6f is closed while maintaining the switch 6g at the closed state. When plasma discharging becomes stable, the switch 6g is opened, and the crowbar circuit switch 6d is closed. Thereafter, the operation of closing the switches 6g and 6f for connecting the capacitor 6c and the operation of closing the crowbar switch 6d are alternately repeated, so that the plasma is continuously formed from the film deposition material gas. Meanwhile, as shown at J in the figure, the electric field is applied in the direction from the central electrode 2 toward the ring-like electrode 3. Also, as indicated by B in the figure, the magnetic field is applied in the opposite directions to upper and lower halves of the interior of the ring-like electrode. These electric field and magnetic field generate the electromagnetic force toward the tube S1. The generated plasma spirally moves to and diffuses at the interior of the tube S1 by this electromagnetic force as shown in the figure, and the intended film is uniformly deposited on the inner peripheral surface of the tube S1 in the plasma.

Figure 2:
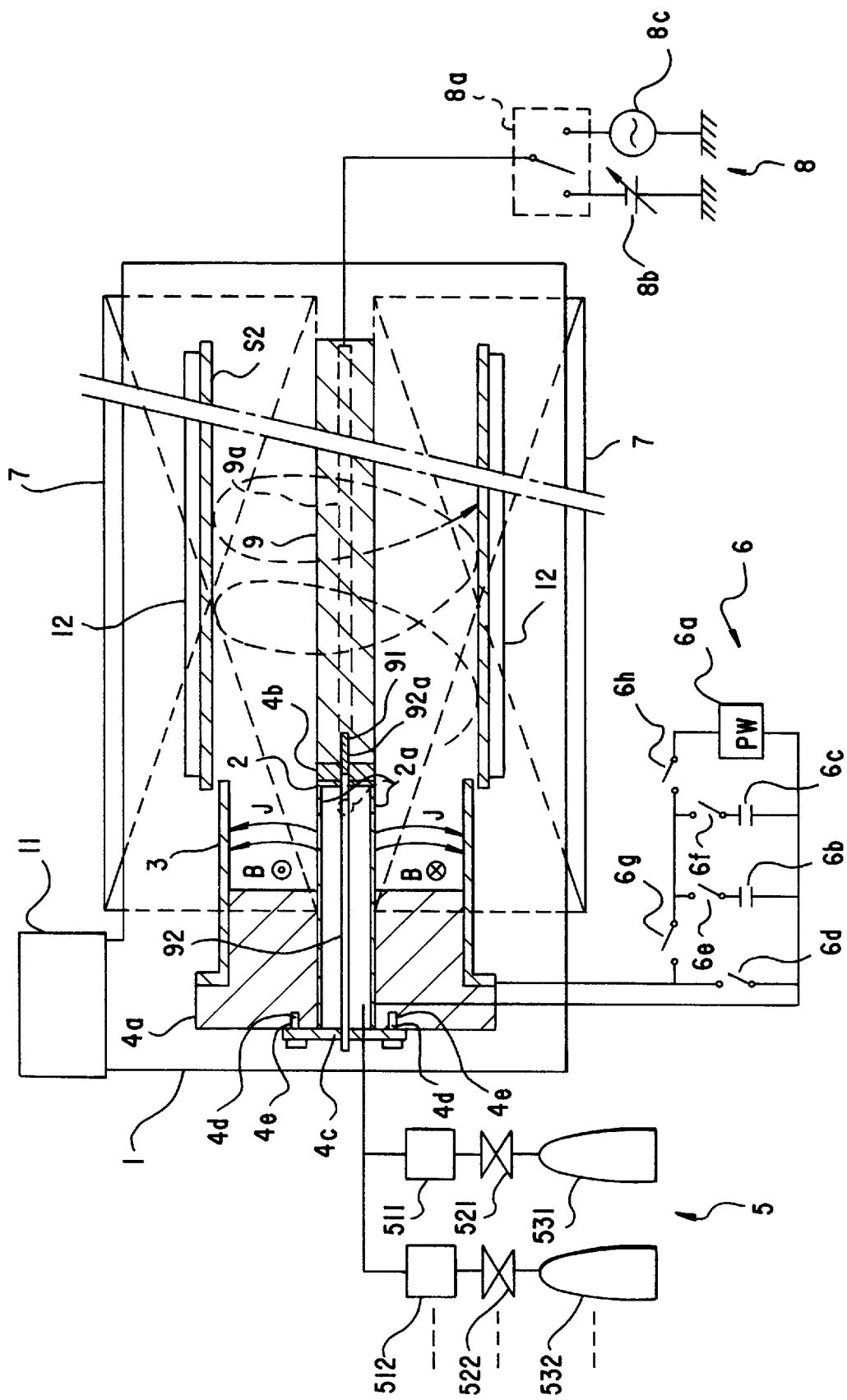
FIG. 2 is a fragmentary cross section schematically showing a structure of another example of an apparatus for manufacturing a tube having a film on its inner peripheral surface.

FIG. 2 shows another embodiment of an apparatus for manufacturing a film on an inner peripheral surface of a tube S2, which differs from the apparatus shown in FIG. 1 in that a solid rod-like sputtering target 9 having a circular section is attached to the end of the central electrode 2 with a ring-like electric insulator 4b therebetween. The sputtering target 9 has a diameter substantially equal to the outer diameter of the central electrode 2, and has a length substantially equal to the length of the tube S2. If the sputtering target 9 is made of an electrical insulator, a rod-like inner electrode 9a having the substantially same length as the target 9 is disposed inside the target 9. The sputtering target 9 is provided at its end adjacent to the insulator 4b with a threaded hole 91, with which an external thread 92a formed at an end of a support rod 92 engages to support the sputtering target 9 in a cantilever manner. The support rod 92 is electrically isolated from the central electrode 2 by the insulator 4b, and extends through the central electrode 2. A rear end of the support rod 92 is fitted into and supported by an electrical insulator 4c covering a rear opening of the insulator 4a. The insulator 4c is fixed to the ring-like insulator 4a by a plurality of bolts 4d screwed into threaded holes 4e formed at the insulator 4a. The sputtering target 9 may be supported by a manner other than the above. For example, the sputtering target 9 may be removably supported at its end remote from the rod-like electrode 2, or may be removably supported at its opposite ends.

For the sputtering target 9, there is provided a power supply 8 which can be connected to the target 9 or inner electrode 9a. The power supply 8 includes a voltage-variable DC power source 8b for applying a negative voltage and a radio-frequency power source 8c, which are selectively connected to the target 9 or inner electrode 9a via a selector switch 8a. Structures other than the above are the same as those of the apparatus shown in FIG. 1. The same parts and portions as those in FIG. 1 bear the same reference numbers. However, in the apparatus in FIG. 2, the gas supply 5 is used as a supply of a plasma source gas for sputtering the target 9. Therefore, the gas sources 531, 532, . . . form plasma gas sources for sputtering the target 9.

According to this apparatus, the solenoid 7 applies the longitudinal magnetic field in the direction indicated by B in the figure to the interior of the ring-like electrode 3. Initially, all the switches in the power supply 6 are open. A tube S2 is transferred into the vacuum container 1, and is supported by the holder 12 such that it is substantially continuous to the ring-like electrode 3. Thereafter, the sputtering target 9 or inner electrode 9a is connected to the power supply 8. Before this connection, however, the selector switch 8a of the power supply 8 was open and thus was connected to neither of the power sources 8b and 8c. Thereafter, the exhaust device 11 is operated to attain the predetermined degree of vacuum in the container 1.

Then, the plasma source gas is introduced from the gas supply 5, and is ejected through the gas nozzles 2a of the central electrode 2 into the space between the electrodes 2 and 3. Also, the power supply 6 applies the DC power between the electrodes 2 and 3 similarly to the apparatus in FIG. 1, so that the plasma is continuously formed from the plasma source gas.

If the sputtering target 9 is made of an electrically conductive material, a negative voltage is applied to the target 9 from the DC power source 8b via the selector switch 8a. If the target 9 is made of an electrical insulator, a radio-frequency voltage is applied to the inner electrode 9a from the radio-frequency power source 8c via the selector switch 8a.

An electromagnetic force is generated toward the tube S2 by the actions of the electric field applied radially toward the ring-like electrode 3 from the central electrode 2 as indicated by J in the figure and the magnetic field applied oppositely in the upper and lower halves of the interior of the ring-like electrode 3 as indicated by B in the figure. The electromagnetic force thus generated acts to move spirally the generated plasma into the tube S2 as shown in the figure.

If the sputtering target 9 is made of an electrically conductive material, ions in the plasma moved into the tube S2 are pulled toward the target 9 to which the negative voltage is applied, so that the target 9 is continuously sputtered. If the target 9 is made of an electrical insulator, accumulation of the charges at the surface of the target 9, which may be caused by the ions in the plasma, is suppressed by the application of the radio-frequency voltage to the inner electrode 9a, and the ions continuously sputter the target 9. In either case, the sputtering particles are continuously deposited uniformly or substantially uniformly on the inner peripheral surface of the tube S2 to form the film.

If an inert gas is used as the plasma source gas, a film consisting of atoms forming the target 9 is formed on the inner peripheral surface of the tube S2. If an active gas such as a nitrogen gas, an ammonia gas or an oxygen gas is used, a film made of nitride or oxide of atoms forming the target is formed on the inner peripheral surface of the tube.

In the above description, the electric field formed by the application of the power supply 6 is directed from the central electrode 2 toward the ring-like electrode 3 as indicated by J in the figure. Alternatively, the electric field may be directed from the ring-like electrode 3 toward the central electrode 2. In this case, the solenoid 7 is operated to form the magnetic field which is applied to the interior of the ring-like electrode 3 in the directions opposite to those indicated by B in the figure, whereby a similar electromagnetic force for moving the plasma toward the tube S2 can be generated.

Figure 3:
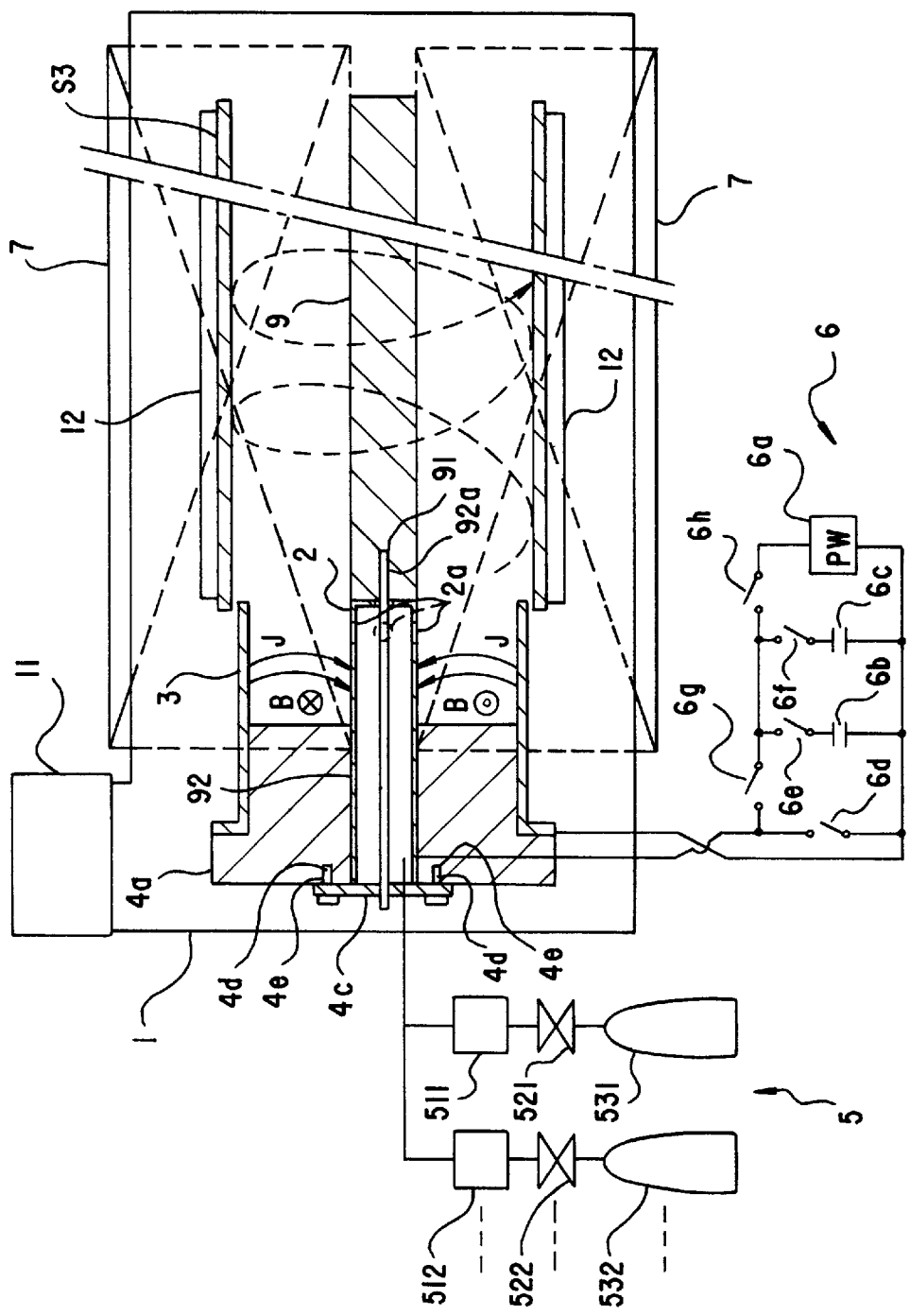
FIG. 3 is a fragmentary cross section schematically showing a structure of still another example of an apparatus for manufacturing a tube having a film on its inner peripheral surface.
Figure 4:
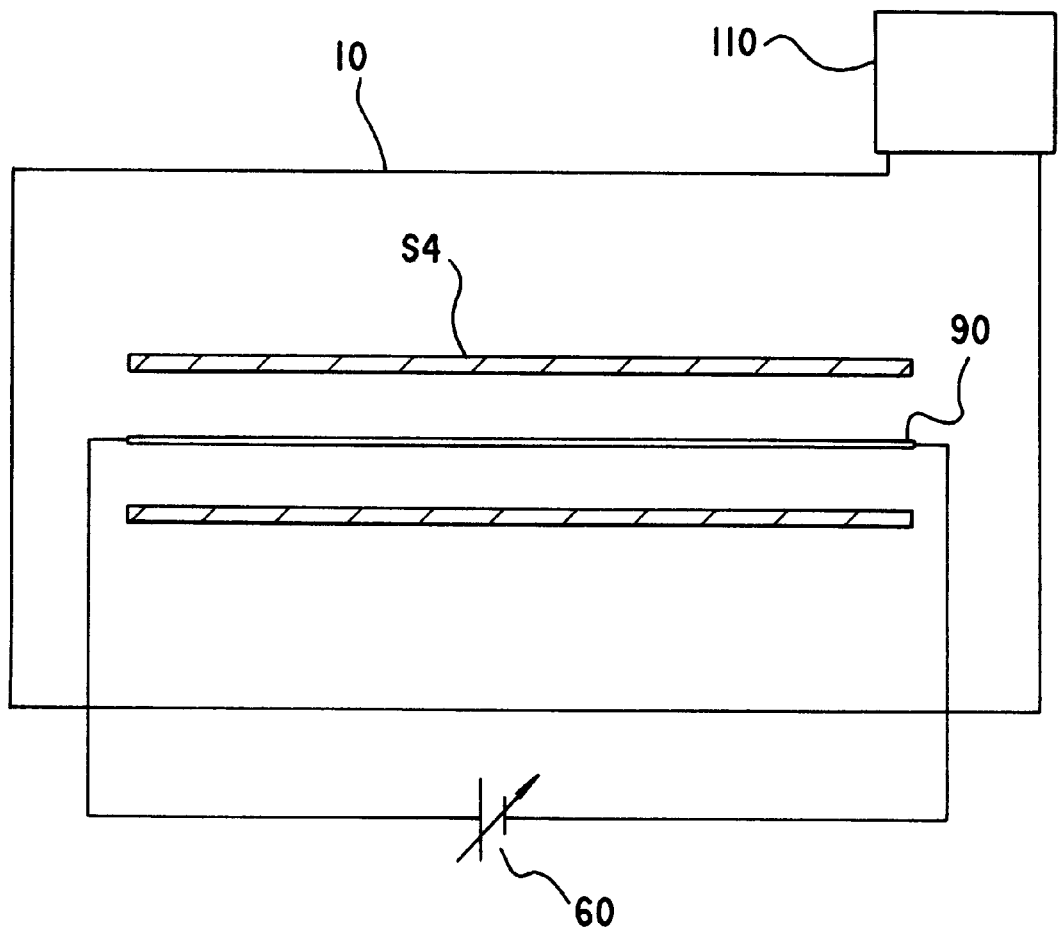
FIG. 4 schematically shows a structure of an apparatus for manufacturing a tube having a film on its inner peripheral surface in the prior art.

FIG. 3 shows still another embodiment of an apparatus for manufacturing a film on an inner peripheral surface of a tube S3, which differs from the apparatus in FIG. 2 in that the sputtering target 9 is in contact with the end of the central electrode 2 without interposing the electrical insulator 4b therebetween, and the power supply 8 is not provided. Further a manner of connection of the electrode 2 and 3 to the power supply 6 as well as the direction of application of the longitudinal magnetic field are also different. Structures other than the above are similar to those of the apparatus in FIG. 2, and the similar parts and portions bear the same reference numbers.

According to this apparatus, the longitudinal magnetic field indicated by B in the figure is applied to the interior of the ring-like electrode 3. Initially, all the switches in the power supply 6 are open. A tube S3 is transferred into the vacuum container 1, and is supported by the holder 12 such that it is substantially continuous to the ring-like electrode 3. Thereafter, the exhaust device 11 is operated to attain the predetermined degree of vacuum in the container 1.

Then, the plasma source gas is introduced into the space between the central electrode 2 and the ring-like electrode 3 similarly to the apparatus in FIG. 2. Also, the power supply 6 applies the DC power directed from the ring-like electrode 3 toward the central electrode 2 so that the plasma is continuously formed from the gas. If the sputtering target 9 is made of an electrically conductive material, the power supply 6 applies a voltage to the sputtering target 9 to attain the same potential as the central electrode 2. If the sputtering target 9 is made of an electrical insulator, a radio-frequency voltage is applied from another unillustrated power supply to an unillustrated rod-like inner electrode which is arranged inside the target 9 and has the substantially same length as the target 9. In this case, the support rod 92 may be made of an electrical insulator or is electrically isolated from the electrode 2, if this is necessary or preferable, for example, due to the fact that the inner electrode is in contact with the support rod 92.

An electromagnetic force is generated toward the tube S3 by the actions of the electric field applied radially from the ring-like electrode 3 toward the central electrode 2 as indicated by J in the figure and the magnetic field applied oppositely in the upper and lower halves of the interior of the ring-like electrode 3 as indicated by B in the figure. The electromagnetic force thus generated acts to move spirally the generated plasma into the tube S3 as shown in the figure.

Similarly to the apparatus shown in FIG. 2, ions in the plasma continuously sputter the target 9, and thus the sputtering particles are continuously deposited uniformly or substantially uniformly on the inner peripheral surface of the tube S3 to form the film.

If the sputtering target 9 is made of an electrical insulator, the electric field J and magnetic field B may be formed in the same directions as those by the apparatus shown in FIG. 2. Even in this case, the electromagnetic force is generated and directed toward the tube S3.

Specific examples of manufacturing of a glass tube provided at its inner peripheral surface with a titanium (Ti) film by the apparatus in FIG. 1 will be described below.

EXAMPLE 1
Size of Glass Tube to be Processed
   10 mm (outer dia.) (inner dia.=9 mm)×1 m (length)
Apparatus Sizes
   Central Electrode 2: 2 mm (dia.)×10 mm (effective discharging length)
   Ring-like Electrode 3: 8 mm (dia.)×8 mm (effective discharging length)
   Gas Nozzle 2a: Diameter=0.5 mm, Number=4
Deposition Conditions
   Deposition Vacuum Pressure: 50 mTorr
   Discharge Start Power: 1 kV, 180 mA
   Deposition Rate Control Power: 1 kV, 10 mA
   Magnetic Field Intensity: 100 Gauss
   Deposition Material Gas: Titanium Tetrachloride (TiCl$_4$), 20 sccm
Deposition Result
   Deposition Time: 2 sec
   Film Thickness (Deposition Rate): 2 $\mu$m (1 $\mu$m/sec)
   Thickness Uniformity: ±10%

EXAMPLE 2
Size of Glass Tube to be Processed
   5 mm (outer dia.) (inner dia.=4 mm)×50 cm (length)
Apparatus Sizes
   Central Electrode 2: 1 mm (dia.)×10 mm (effective discharging length)
   Ring-like Electrode 3: 3 mm (dia.)×8 mm (effective discharging length)
   Gas Nozzle 2a: Diameter=0.2 mm, Number=4
Deposition Conditions
   Deposition Vacuum Pressure: 50 mTorr
   Discharge Start Power: 1 kV, 150 mA
   Deposition Rate Control Power: 1 kV, 10 mA
   Magnetic Field Intensity: 100 Gauss
   Deposition Material Gas: Titanium Tetrachloride (TiCl$_4$), 10 sccm
Deposition Result
   Deposition Time: 2 sec
   Film Thickness (Deposition Rate): 1.5 $\mu$m (0.75 $\mu$m/sec)
   Thickness Uniformity: ±10%

EXAMPLE 3
Size of Glass Tube to be Processed
   2 mm (outer dia.) (inner dia.=1.4 mm)×10 cm (length)
Apparatus Sizes
   Central Electrode 2: 0.5 mm (dia.)×10 mm (effective discharging length)
   Ring-like Electrode 3: 1.0 mm (dia.)×8 mm (effective discharging length)
   Gas Nozzle 2a: Diameter=0.2 mm, Number=2
Deposition Conditions
   Deposition Vacuum Pressure: 50 mTorr
   Discharge Start Power: 1 kV, 120 mA
   Deposition Rate Control Power: 1 kV, 10 mA
   Magnetic Field Intensity: 100 Gauss
   Deposition Material Gas: Titanium Tetrachloride (TiCl$_4$), 5 sccm
Deposition Result
   Deposition Time: 2 sec
   Film Thickness (Deposition Rate): 1 $\mu$m (0.5 $\mu$m/sec)
   Thickness Uniformity: ±20%

Specific examples of manufacturing of a glass tube provided at its inner peripheral surface with a film by the apparatus in FIG. 2 will be described below.

EXAMPLE 4
Formation of a Titanium (Ti) Film
Size of Glass Tube to be Processed
   20 mm (outer dia.) (inner dia.=19 mm)×1 m (length)
Apparatus Sizes
   Central Electrode 2: 6 mm (dia.)×10 mm (effective discharging length)
   Gas Nozzle 2a: Diameter=0.5 mm, Number=4
   Ring-like Electrode 3: 18 mm (dia.)×8 mm (effective discharging length)
   sputtering target 9: 6 mm (dia.)×1.2 mm (length)
   Circular Titanium (Ti) Rod
Deposition Conditions
   Deposition Vacuum Pressure: 5 mTorr
   Discharge Start Power: 1 kV, 180 mA
   Deposition Rate Control Power: 1 kV, 10 mA
   sputtering target Application Voltage: DC −600V
   Magnetic Field Intensity: 100 Gauss
   Plasma Source Gas: Argon (Ar) gas, 5 sccm
Deposition Result
   Deposition Time: 2 sec
   Film Thickness (Deposition Rate): 1.6 $\mu$m (0.8 $\mu$m/sec)
   Thickness Uniformity: ±10%

EXAMPLE 5
Formation of a Silicon Dioxide (SiO$_2$) Film
Size of Glass Tube to be Processed
   20 mm (outer dia.) (inner dia.=19 mm)×1 m (length)
Apparatus Sizes
   Central Electrode 2: 6 mm (dia.)×10 mm (effective discharging length)
   Gas Nozzle 2a: Diameter=0.5 mm, Number=4
   Ring-like Electrode 3: 18 mm (dia.)×8 mm (effective discharging length)
   sputtering target 9: 6 mm (dia.)×1.2 mm (length)
   Circular Silicon (Si) Rod
Deposition Conditions
   Deposition Vacuum Pressure: 5 mTorr
   Discharge Start Power: 1 kV, 200 mA
   Deposition Rate Control Power: 1 kV, 18 mA
   sputtering target Application Voltage: DC −450V
   Magnetic Field Intensity: 100 Gauss
   Plasma Source Gas: Oxygen (O$_2$) gas 5 sccm
   Argon (Ar) gas, 5 sccm
Deposition Result
   Deposition Time: 2 sec
   Film Thickness (Deposition Rate): 1.0 $\mu$m (0.5 $\mu$m/sec)
   Thickness Uniformity: ±10%

EXAMPLE 6
Formation of a Titanium Nitride Film
Size of Glass Tube to be Processed
   20 mm (outer dia.) (inner dia.=19 mm)×1 m (length)
Apparatus Sizes
   Central Electrode 2: 6 mm (dia.)×10 mm (effective discharging length)
   Gas Nozzle 2a: Diameter=0.5 mm, Number=4
   Ring-like Electrode 3: 18 mm (dia.)×8 mm (effective discharging length)
   sputtering target 9: 6 mm (dia.)×1.2 m (length)
   Circular Titanium (Ti) Rod
Deposition Conditions
   Deposition Vacuum Pressure: 5 mTorr
   Discharge Start Power: 1 kV, 150 mA
   Deposition Rate Control Power: 1 kV, 8 mA
   sputtering target Application Voltage: DC −400V
   Magnetic Field Intensity: 100 Gauss Deposition Material Gas: Nitrogen (N$_2$) gas, 5 sccm Argon (Ar) gas, 5 sccm Deposition Result Deposition Time: 2 sec Film Thickness (Deposition Rate): 1.0 μm (0.5 μm/sec)

Thickness Uniformity: ±10%

From the aforementioned results, it can be found that even if the tube has a small inner diameter and/or has a large length relatively to the inner diameter, the film can be deposited on the inner peripheral surface uniformly or substantially uniformly within a short time.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of manufacturing a tube having a film on an inner peripheral surface thereof comprising the steps of:

disposing a hollow rod-like electrode provided with a gas nozzle in a vacuum container;

disposing a ring-like electrode around said rod-like electrode with a predetermined space therebetween;

disposing a tube to be processed such that said tube is substantially continuous to said ring-like electrode;

setting an interior of said vacuum container to a predetermined degree of vacuum for deposition;

introducing a deposition material gas into a space between said rod-like and ring-like electrodes through said gas nozzle of said rod-like electrode;

applying electric power for forming plasma from said gas while applying a magnetic field around said vacuum container; and supplying the produced plasma into said tube for forming said film on said inner peripheral surface of said tube in the plasma.

2. A method of manufacturing a tube having a film on an inner peripheral surface thereof comprising the steps of:

disposing a hollow rod-like electrode provided with a gas nozzle in a vacuum container;

disposing a ring-like electrode around said rod-like electrode with a predetermined space therebetween;

disposing a rod-like sputtering target receiving a voltage on an extension of said rod-like electrode;

disposing a tube to be processed such that said tube is located around said sputtering target and is substantially continuous to said ring-like electrode;

setting an interior of said vacuum container to a predetermined degree of vacuum for deposition;

introducing a plasma source gas into a space between said rod-like and ring-like electrodes through said gas nozzle of said rod-like electrode;

applying electric power for forming plasma from said gas while applying a magnetic field around said vacuum container;

supplying the produced plasma into said tube; and applying a sputtering voltage to said sputtering target for sputtering said sputtering target to form said film on said inner peripheral surface of said tube.

3. An apparatus for manufacturing a tube having a film on an inner peripheral surface thereof, said apparatus comprising:

a vacuum container;

a hollow rod-like electrode which is provided with a gas nozzle and disposed in said vacuum container and a ring-like electrode disposed in said vacuum container and around said rod-like electrode with a predetermined space therebetween;

a holder holding a tube to be processed such that said tube is substantially continuous to said ring-like electrode;

gas introducing means for introducing a deposition material gas into a space between said rod-like and ring-like electrodes through said gas nozzle of said rod-like electrode;

electric power applying means for applying electric power between said electrodes to produce plasma from said gas; and magnetic field applying means for applying a magnetic field to said plasma so as to supply said plasma generated between said electrodes into said tube held by said holder, said magnetic field applying means disposed around said vacuum container.

4. An apparatus for manufacturing a tube having a film on an inner peripheral surface thereof, said apparatus comprising:

a vacuum container;

a hollow rod-like electrode which is provided with a gas nozzle and disposed in said vacuum container and a ring-like electrode disposed in said vacuum container and around said rod-like electrode with a predetermined space therebetween;

supporting means for supporting a rod-like sputtering target on an extension of said rod-like electrode;

a holder for holding a tube to be processed around said sputtering target supported by said supporting means such that said tube is substantially continuous to said ring-like electrode;

gas introducing means for introducing a plasma source gas into a space between said rod-like and ring-like electrodes through said gas nozzle of said rod-like electrode;

electric power applying means for applying electric power between said electrodes to produce plasma from said gas;

magnetic field applying means for applying a magnetic field to said plasma so as to supply said plasma generated between said electrodes into said tube held by said holder, said magnetic field applying means disposed around said vacuum container; and sputtering voltage applying means for applying a sputtering voltage to said sputtering target.

* * * * *